United States Patent [19]
Lasaitis et al.

[11] Patent Number: 5,449,350
[45] Date of Patent: Sep. 12, 1995

[54] INTRAVENOUS FLUID ADMINISTRATION DEVICE CONTAINING ANTI-SQUIRTING ORIFICE FLOW CONTROL

[75] Inventors: Con A. Lasaitis, Waukegan; Robert J. Kruger, McHenry, both of Ill.

[73] Assignee: Abbott Laboratories, Abbott Park, Ill.

[21] Appl. No.: 276,980

[22] Filed: Jul. 19, 1994

[51] Int. Cl.$^6$ .............................. A61M 5/00
[52] U.S. Cl. ........................ 604/246; 138/40; 138/44; 138/42
[58] Field of Search .................. 138/37, 40, 42, 44, 138/46; 239/590, 590.5; 604/246, 204

[56] References Cited

U.S. PATENT DOCUMENTS

| | | | |
|---|---|---|---|
| Re. 25,173 | 5/1962 | Fraser | 138/40 |
| 67,614 | 8/1867 | Trees | 138/40 |
| 894,558 | 7/1908 | Wheaton | 239/590 |
| 1,242,359 | 10/1917 | McKenna | 239/590 |
| 1,502,687 | 7/1924 | Sendig | 138/40 |
| 1,720,245 | 7/1929 | Smith | 138/42 |
| 1,812,916 | 7/1931 | Zerk | 138/42 |
| 1,964,836 | 7/1934 | Wheaton | 239/590 |
| 1,968,348 | 7/1934 | Plaude | 239/590.5 |
| 2,111,991 | 3/1938 | Richard | 138/40 |
| 2,271,982 | 2/1942 | Van Kreveld | 138/44 |
| 2,408,588 | 10/1946 | Watts | 239/590.5 |
| 2,423,960 | 7/1947 | Bucknell et al. | 239/590.5 |
| 2,562,930 | 8/1951 | Mapes | 239/590 |
| 2,580,722 | 1/1952 | Bentley | 239/590.5 |
| 2,602,701 | 7/1952 | Walter | 138/40 |
| 2,604,110 | 7/1952 | Gilder | 138/40 |
| 2,809,073 | 10/1957 | Wahlert | 239/590 |
| 2,988,288 | 6/1961 | Nielsen | 239/590.5 |
| 3,188,521 | 6/1965 | Hart | 361/215 |
| 3,726,482 | 4/1973 | Heinrichs | 239/590.5 |
| 3,744,762 | 7/1973 | Schlicht | 138/42 |
| 3,749,130 | 7/1973 | Howitt et al. | 138/42 |
| 3,982,157 | 9/1976 | Azuma et al. | 361/215 |
| 4,128,206 | 12/1978 | Bintner | 239/590 |
| 4,269,186 | 5/1981 | Loveless et al. | 138/40 |
| 4,466,462 | 8/1984 | Morris | 138/42 |
| 4,576,204 | 3/1986 | Smallhorn et al. | 138/40 |
| 5,099,881 | 3/1992 | Nakajima | 138/40 |
| 5,315,859 | 5/1994 | Schommer | 138/44 |

FOREIGN PATENT DOCUMENTS

| | | | |
|---|---|---|---|
| 136933 | 5/1947 | Australia | 239/590.5 |
| 712658 | 9/1941 | Germany | 239/590.5 |
| 1198774 | 12/1985 | U.S.S.R. | 361/215 |

Primary Examiner—James E. Bryant, III
Attorney, Agent, or Firm—Thomas M. Breininger; Brian R. Woodworth

[57] ABSTRACT

A flow control device for a liquid agent administration apparatus includes a body. The body has an inlet port, an outlet passage, and a flow control orifice between the inlet port and outlet passage. A deflection surface is located within the outlet passage and is spaced from the orifice to be impinged by a stream of the liquid discharging from the orifice.

18 Claims, 2 Drawing Sheets

INTRAVENOUS FLUID ADMINISTRATION DEVICE CONTAINING ANTI-SQUIRTING ORIFICE FLOW CONTROL

TECHNICAL FIELD

This invention relates to infusion systems for the administration of solutions or other liquid agents for patient care and more particularly to a solution administration apparatus including an orifice flow restrictor for providing flow under varying pressure and fluid viscosity conditions.

BACKGROUND OF THE INVENTION AND TECHNICAL PROBLEMS POSED BY THE PRIOR ART

Inpatient and outpatient therapy often requires the administration of an intravenous solution or other liquid agent to a patient through a device such as a catheter to permit infusion of a solution, medicament, or other liquid agent as required. The rate of flow of solution into the patient's body is an important variable which can be affected by the pressure of the solution supply and the fluid viscosity.

A system for administering a liquid agent to a patient is disclosed in the commonly assigned, copending U.S. patent application Ser. No. 08/125,979 filed Sep. 23, 1993.

The administration system accommodates infusion with a controlled, predetermined fluid flow. The system includes a solution or other liquid agent supply container, a tubing set, and a laser drilled orifice flow restrictor.

The supply container may be a collapsible bag for the self-contained, pressurized type of mobile patient solution administration. The supply container has a fluid port to which is connected a tubing set that includes a length of tubing. A restrictor body and housing is mounted to the end of the tubing. An orifice is located within the body interior. The housing includes a typical snap-nut Luer lock fitting connector. The male end is in fluid connection with the tubing set. The female fitting of the Luer lock connector can be connected in fluid communication with a catheter for patient infusion of the solution or other agent.

The orifice is a generally cylindrical, small diameter passage drilled by laser through a wall or plate of the restrictor which creates a boundary between the inlet and outlet ports of the restrictor. The passage has a predetermined cross-sectional flow area and defines a flow control passage. The restrictor also defines an outlet passage downstream of the flow control orifice.

The orifice plate is relatively thin. However, the thickness is dependent upon the diameter of the orifice drilled therethrough. The actual orifice diameter will vary as required by the precise flow of solution for the particular patient's requirements.

The orifice flow restrictor delivers a predetermined and accurate flow of solution to a patient. Unlike capillary restrictors, the orifice restrictor is relatively unaffected by minor variations in supply solution pressure or viscosity. Moreover, because of the interrelationship between solution feed viscosity and temperature, the orifice restrictor is also relatively unaffected by minor variations in temperature as well.

Although the above-described administration system functions well in many applications, it would be desirable to provide an improved system that could be used to accommodate use with pressurized cuff solution feed containers and/or that would provide an improved priming capability.

For example, in order to administer the liquid agent, the flexible container is inserted into a conventional pressurization cuff. Before the tubing is connected to the catheter, the cuff is pressurized to force the liquid agent out of the container and through the tubing to bleed air from the tubing and other components (e.g., filters, valves, and fittings) until the liquid agent fills the entire system.

Typically, before connecting the administration set to the catheter, the patient bleeds and primes the system by pressurizing the cuff and watching for a drop of the liquid agent to be discharged from the end fitting on the tubing as an indication that all of the air has been bled out of the system. If the end fitting employed on the tubing is the above-described flow restrictor, then some of the pressurized liquid agent can be forced out of the flow control orifice following the last portion of the air being bled out of the system.

Under high cuff pressures, the liquid agent may have a tendency to squirt or stream out of the orifice (prior to the restrictor housing being connected to the catheter). This may result in the undesirable loss of some of the liquid agent. If the system is misused or not otherwise handled in accordance with proper procedures, then unnecessary and undesirable contact between the fluid and the patient may occur prior to the restrictor housing being connected to the catheter.

Accordingly, it would be desirable to provide an improved system which would prevent or minimize streaming or squirting of a liquid agent from the restrictor housing, at least prior to connection of the restrictor housing with the catheter.

It would also be desirable to provide an improved system which could function over a range of low and high pressures.

Additionally, it would be beneficial if such an improved system could be embodied in designs having a relatively low manufacturing cost and a relatively high operational reliability.

The present invention provides an improved flow control device which can accommodate designs having the above-discussed benefits and features.

SUMMARY OF THE INVENTION

The present invention provides a flow control device for use in administration systems for accommodating infusion with a controlled, pre-determined fluid flow. The flow control device permits use of administration equipment with a pressurizable cuff or other system for pressurizing a liquid.

The flow control device is effective in preventing or minimizing squirting or streaming, and this is especially advantageous during the initial priming of the system to bleed off air from the system. This minimizes the loss of liquid agent and minimizes the likelihood of the patient unnecessarily contacting the liquid agent.

The flow control device includes a body. The body has (1) an inlet port (2) an outlet passage, and (3) a flow control orifice establishing communication between the inlet port and the outlet passage. Fluid communication can be established between the inlet port and a supply of liquid agent and between the outlet passage and the patient (e.g., via a catheter).

A deflection surface is located within the outlet passage. The deflection surface is spaced from the orifice so as to be impinged by a stream of the liquid agent discharging from the orifice. This breaks up the stream, and prevents the liquid agent from squirting out of the device. The structure defining the deflection surface also serves to reduce the internal volume that must be pressurized without otherwise adversely affecting the operating flow and without deforming or breaking off.

It is to be understood that the flow control orifice can include restricted pathways created by, for example, laser drilling, molding such as insert molding a capillary, or other manufacturing techniques of forming holes, capillaries or other restricted pathways in various materials.

Numerous other advantages and features of the present invention will become readily apparent from the following detailed description of the invention, from the claims, and from the accompanying drawings.

BRIEF DESCRIPTION OF THE DRAWINGS

In the accompanying drawings that form part of the specification, and in which like numerals are employed to designate like parts throughout the same, FIG. 1 is a simplified plan view of a solution (or other liquid agent) administration system with the flow control device of the present invention;

FIG. 2 is a greatly enlarged, perspective, partial cross-sectional view of the flow control device of the present invention;

FIG. 3 is a greatly enlarged, end view of an insert member which is adapted to be inserted into the flow control device housing;

FIG. 4 is an end view of an alternate embodiment of an insert member;

FIG. 5 is an end view of another alternate embodiment of an insert member; and FIG. 6 is a view similar to FIG. 2, but FIG. 6 illustrates a further modification of the flow control device.

DESCRIPTION OF THE PREFERRED EMBODIMENTS

While this invention is susceptible of embodiment in many different forms, this specification and the accompanying drawings disclose only some specific forms as examples of the invention. The invention is not intended to be limited to the embodiments so described, however. The scope of the invention is pointed out in the appended claims.

The device of this invention is used with certain conventional components the details of which, although not fully illustrated or described, will be apparent to those having skill in the art and an understanding of the necessary functions of such components.

Referring now to the drawings, the general arrangement of a contemplated typical arrangement of an administration system incorporating the flow control device of the present invention can be best understood with reference to FIG. 1. One such system that may be employed with the present invention is described in the above-identified U.S. patent application Ser. No. 08/125,979 which is incorporated herein by reference thereto to the extent not inconsistent herewith.

The system includes an orifice flow restrictor 12, a tubing set 14, an in-line slide clamp 16, a conventional air elimination filter 18, a Y-injection site connector 20, a conventional port connector 19, and an associated liquid agent or solution supply container 22, as shown by the exemplary intravenous solution supply bag fabricated from a flexible thermoplastic material.

The container or bag 22 is disposed in a pressurization cuff 23 which can be hung with a clip 21 from patient clothing (not shown) and which can be pressurized in a well-known manner so as to force the liquid agent from the bag 22 through the tubing set 14.

The air elimination filter 18 can be operably interposed anywhere in tubing set 14 between flow restrictor 12 and bag 22.

Referring now to FIG. 2, the orifice flow control device 12 of the present invention is shown more fully in detail. The device 12 includes an elongated body 24 with an inlet port 26 and an outlet port 28 formed therein. The body 24 is preferably fabricated from a synthetic polymer material. Separating the inlet and outlet ports 26, 28 is a barrier-like wall or orifice plate 30.

The inlet end of the body 24 has first, second, and third inward tapered passages 32, 34, and 36, respectively. The tube end of the tubing set 14 is received in the passages and is compressively engaged in the passage 36. The tubing is also preferably solvent bonded within the passage 36.

The passage 36 has a distal portion with a plurality of raised, longitudinal ribs 40 (four in a currently contemplated embodiment) which are equally spaced around the longitudinal axis of the body 24. The distal end of the tubing abuts the proximal ends of the ribs 40.

The distal ends of the ribs 40 terminate at, and merge with, the orifice wall or plate 30. The proximal side of the plate 30 is formed with a tapered nipple-shaped depression 44 therein. The distal side of the orifice wall 30 defines a flat surface 50.

An orifice 48 is drilled through the plate 30, and the orifice 48 defines a flow control passage which extends from about the center of depression 44 to an outlet passage 49 inwardly of the outlet port 28. The passage 49 is preferably tapered (i.e., frustoconical) and has its largest diameter at the outlet port 28.

The orifice 48 has a predetermined cross-sectional flow area which provides accurate, predetermined flow communication between the inlet port 26 and the outlet port 28. Orifice 48 can be produced by drilling through the plate 30 with a laser or other narrow frequency light emitting cutting device. The diameter of orifice 48 typically ranges from about 0.0011 inches to about 0.0080 inches dependent upon the rate of administration of solution as required for the particular application.

In one embodiment of the orifice flow restrictor 12 shown in the associated figures, the body 24 is preferably fabricated from a polycarbonate material. The orifice 48 is drilled to a diameter of 0.003 inches through the orifice plate 30 and has a length of 0.012 inches with a tolerance of $\pm$0.002 inches. The orifice 48 can be drilled using a Resonetics eximer laser. The ratio of the thickness of the plate 30 (between the base of depression 44 and the downstream surface 50 of the plate 30) to the diameter of orifice 48 is preferably limited to a maximum of 10:1. Conversely, the diameter of the orifice 48 is preferably at least one tenth of its length.

According to one aspect of the present invention, an insert member 52 is disposed within the outlet passage 49 as shown in FIG. 2. The inset member 52 is preferably extruded from a thermoplastic polymer. In the preferred embodiment illustrated, the insert member 52 has two oppositely facing end surfaces, an end surface 54 facing out of the body passage 49, and an end surface 56 facing toward the orifice 48. In the preferred embodiment illustrated, the end surface 56 is generally flat and defines an impingement surface or deflection surface spaced from the distal end of the orifice 48. In a preferred embodiment, the deflection surface 56 is spaced about 0.094 inches from the distal end of the orifice 48.

The insert member 52 extends along the outlet passage 49 toward, but not beyond, the outlet port 28. In a preferred, contemplated embodiment, the end surface 54 is generally planar.

FIG. 3 illustrates an end view of the deflection surface 56 of the insert member 52. In the embodiment illustrated in FIG. 3, the insert member 52 includes three ribs 60 which are equally spaced around the periphery of the member 52. The ribs 60 all terminate on a circular locus relative to a central, longitudinal axis 62 which is defined by the insert member and which is coincident with the longitudinal axis of the cylindrical orifice 48. The deflection surface 56 may also be characterized as at least including a generally circular area extending to the ribs 60.

Preferably, the insert member 52 is extruded from polypropylene, and the circular locus defined by the radially outwardmost extension of each rib 60 has a diameter that is greater than the smallest diameter of the frustoconical outlet passage 49. Preferably, the diameter defined by the ribs 60 is even slightly greater than the maximum diameter of the frustoconical outlet passage 49 at the outlet port 28.

In a presently contemplated embodiment, the diameter defined by the ribs is about 0.005 inches greater than the diameter of the outlet passage 49 at the outlet port 28. Thus, when the insert member 52 is inserted into the passage 49, the ribs 60 will be deformed or crushed somewhat (but will not shear or fragment) to establish a strong friction fit. The elongate nature of the insert 52 provides sufficient frictional engagement to maintain the insert within the passage 49 even Over a relatively long shelf life (e.g., two years). During that time, the polypropylene material of the member 52 will be subjected to some amount of cold flow which tends to decrease the outwardly directed resilient forces of the ribs 60. 10 When the insert member 52 is fully inserted and properly positioned, the deflection surface 56 prevents the liquid from squirting from the orifice 48 as a stream beyond the distal end of the restrictor body 24. Although the end surface or deflection surface 56 is spaced from the orifice (e.g., 0.09 inches from the orifice in a presently contemplated embodiment), the surface 56 is sufficiently large to block the stream squirting from the orifice.

In a presently contemplated embodiment, the deflection surface 56 encompasses at least a circular area having a diameter of about 0.05 inches, and this is preferably substantially larger than the diameter of the orifice (e.g., which in a presently contemplated embodiment is about 0.003 inches). The larger diameter area of the end surface 56 also accommodates manufacturing variations and tolerances. Thus, even if the insert member 52 is not aligned exactly on the longitudinal axis of the orifice 48, and even if there are variations in the curvature of the outlet passage 49, in the size of the deflection surface 56, or in the radial extent of the ribs 60, the liquid stream will still impinge on the deflection surface 56 and will not squirt in a stream out of the body 24.

Figure 1:
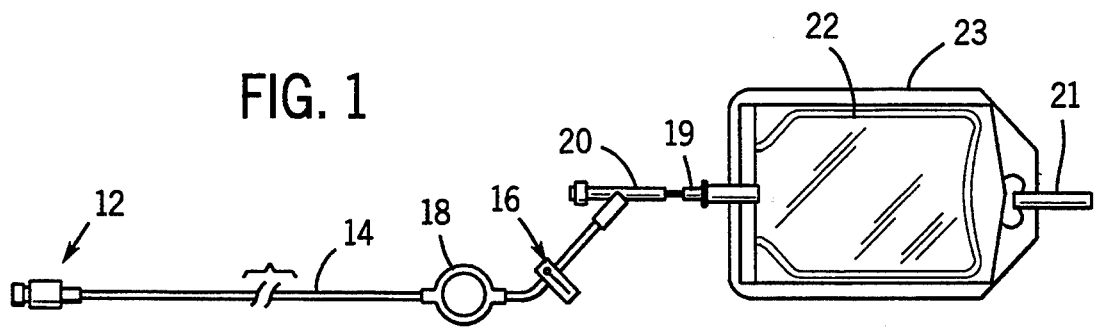

The restrictor body 24 includes a flange 66 projecting radially from the body between the inlet 26 and outlet 28. The flange 66 accommodates mounting of the restrictor body 24 within a housing 70. The housing 70 may be provided in the form snap nut Luer lock having an internal cavity 72 for receiving the body 24 and flange 66. The housing 70 is sufficiently resilient to accommodate insertion of the body 24 in the position illustrated in FIG. 2. The proximal portion of the housing 70 includes a reduced diameter cavity 74 terminating within the housing in an annular lip or shoulder 76 against which the body flange 66 is disposed.

The cavity 74 terminates at the body proximal end in an annular surface 78 against a shoulder 80 defined by an annular rib 82 on the proximal end of the restrictor insert body 24. An annular flange 86 extends distally from the shoulder 80 on the body 24 and is received within the housing cavity 74. The mounting arrangement of the restrictor body 24 within the housing 70 prevents axial movement but permits independent rotational movement of the housing 70 relative to the restrictor body 24.

The distal end of the housing 70 defines a thread form 90 on the wall of the cavity 72 to accommodate a Luer lock engagement with a mating fitting (not shown) on a catheter extending to the patient.

The present invention accommodates design variations with respect to the insert member 52 and restrictor body 24 as well as with respect to the housing 70.

Typically, the restrictor 12, comprising the housing 70, body 24, and insert member 52, would be provided as part of an administration set including the tubing set 14, air elimination filter 18, slide clamp 16, Y-injection site connector 20, port connector 19, and the pressurizing cuff 23. To use the set, the patient obtains the solution or other liquid agent in a new flexible container 22 which is then disposed within the pressurizing cuff 23. The administration set is next connected to the container 22 with the port connector 19. The cuff 23 is then pressurized, and the slide clamp 16 is opened to bleed air from the system and fill the system with the liquid agent.

When a drop of the liquid agent is observed at the outlet port 28 of the restrictor 12, the patient knows that the system has been primed. The housing 70 can then be connected to the catheter, and administration of the intravenous solution or other liquid agent can begin. Because the insert member 52 prevents squirting or streaming of the liquid agent beyond the restrictor 12, the potential for the loss of liquid or unnecessary contact with the liquid is eliminated or minimized.

Figure 6:
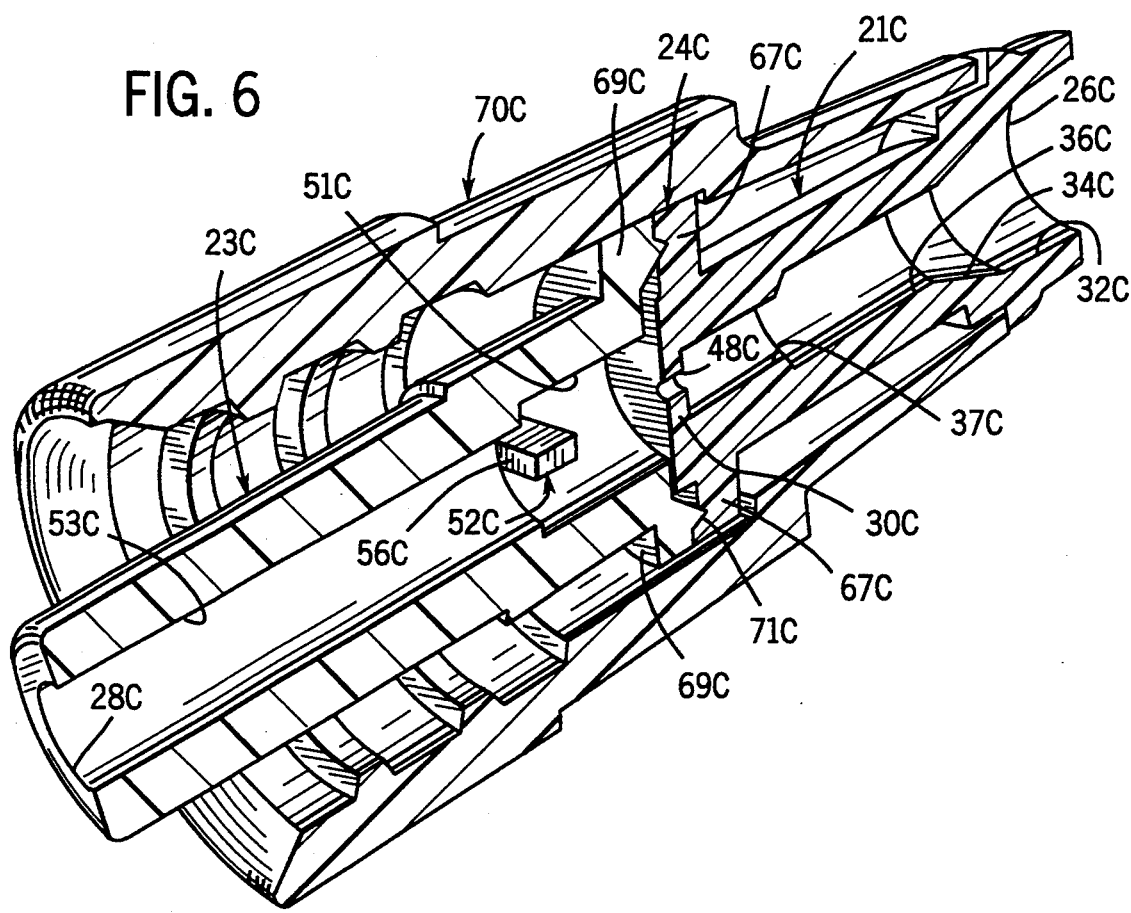

An alternate embodiment of the invention is illustrated in FIG. 6 wherein a two-piece restrictor body 24C is mounted within a housing 70C. The housing 70C has substantially the same configuration as the housing 70 described above with reference to FIG. 2.

The two-piece restrictor body 24C includes a proximal portion 21C and a distal portion 23C. The proximal portion 21C includes a flange 67C, and the distal portion 23C includes a flange 69C. The flange 69C has a welding rib 71C which faces toward the flange 67C and which is ultrasonically welded to the flange 67C.

The proximal portion 21C also defines an interior set of passages 32C, 34C, and 36C. These passages are substantially identical to the passages 32, 34, and 36 described above with reference to the embodiment of the restrictor body 24 illustrated in FIG. 2. The proximal end of the passage 32C terminates in an inlet port 26C.

Figure 2:
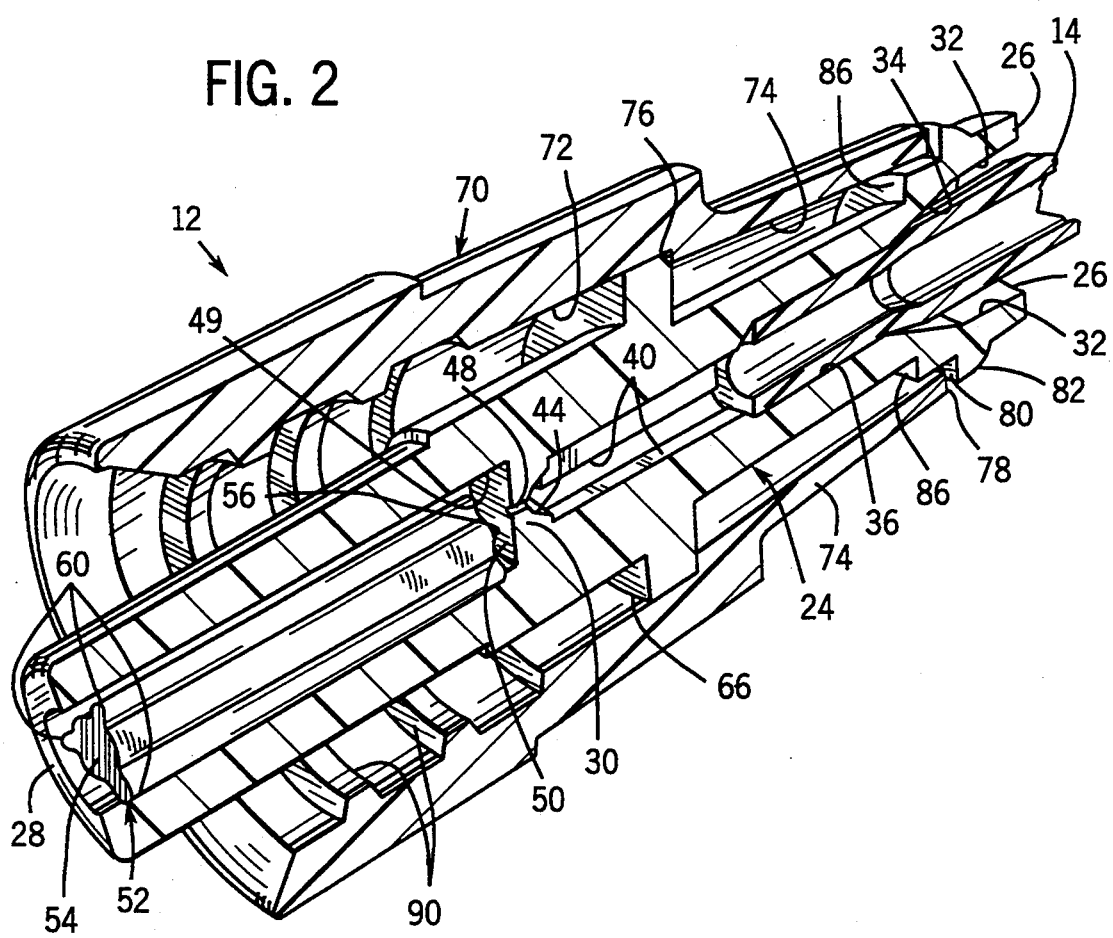
Figure 3:
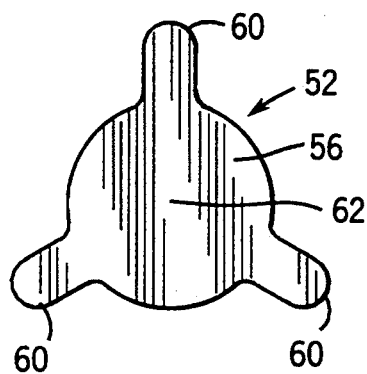
Figure 4:
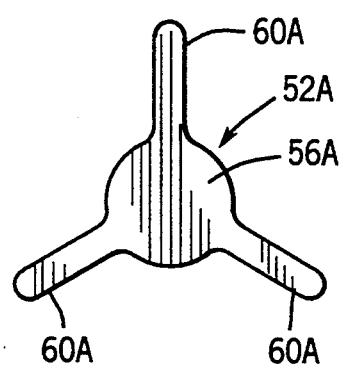
FIG. 4 shows an alternate embodiment of an insert member 52A which has an end surface 56A against which the liquid stream impinges. The insert member 52A includes three ribs 60A which each have a transverse (radial) dimension greater than the transverse dimension of the ribs 60 described above with reference to FIG. 3.
Figure 5:
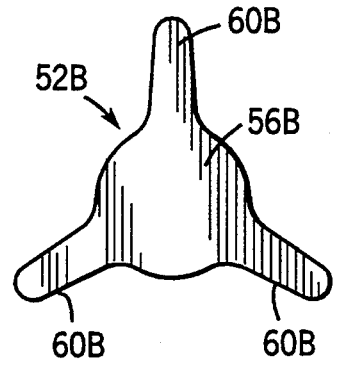
FIG. 5 illustrates another embodiment of an insert member 52B having a deflection surface 56B and three ribs 60B. Each rib 60B, when viewed from the end, decreases in width from its base toward its distal end.

The passages 32C, 34C, and 36C accommodate the insertion of the end of a tube, such as tube 14 illustrated in FIG. 2. The tube 14 may be held within the body portion 21C by means of frictional engagement and/or with a solvent bond or other suitable securing means.

A further passage 37C has a reduced diameter compared to the passage 36C and extends from the passage 36C distally to a restriction wall or orifice plate 30C which is defined by the distal end of the body portion 21C. A flow restriction orifice 48C is defined in the wall 30C.

The body portion 23C defines an interior cylindrical passage 51C opening to the orifice plate 30C and orifice 48C. Extending radially inwardly from the wall of the passage 51C is a generally rectangular tab 52C. The tab 52C has an impingement surface or deflection surface 56C facing the orifice 48C.

The body portion 23C also defines a reduced diameter passage 53C communicating with the passage 51C and extending distally to an outlet port 28C.

The two-piece restrictor body 24C is disposed within the housing 70C in substantially the same way that the first embodiment of the restrictor body 24 is disposed within the housing 70 described above with reference to FIG. 2.

The tab 52C may be molded as a unitary part of the restrictor body portion 23C. Alternatively, the tab 52C may be provided as a separately attached member. Further, the shape and size of the tab 52C may be varied so long as there is a sufficient impingement surface 56C in front of the orifice 48C so as to deflect and disperse the liquid stream exiting from the orifice 48C.

It will be readily apparent from the foregoing detailed description of the invention and from the illustrations thereof that numerous variations and modifications may be effected without departing from the true spirit and scope of the novel concepts or principles of this invention.

What is claimed is:

1. An intravenous fluid administration system comprising:
    an intravenous fluid reservoir;
    a tube having a capacity to transport an intravenous fluid therethrough from a first end portion of said tube to a second end portion of said tube, said first end portion of said tube being fluidly connected to said intravenous fluid reservoir;
    a flow restrictor fluidly connected to said second end portion of said tube, said flow restrictor comprising a body defining a fluid passage therethrough, said fluid passage defined through said body having a first end portion, a second end portion, and an intermediate, flow control portion, said first end portion of said passage being in fluid communication with said second end portion of said tube, said second end portion being distal said first end portion, and said intermediate, flow control portion being disposed between said first end portion and said second end portion, said first end portion of said passage defined through said body having a first diameter at a position proximate said intermediate, fluid control portion, said second end portion of said passage defined through said body having a second diameter at a position proximate said intermediate, fluid control portion, and said intermediate, flow control portion of said passage defined through said body having a third diameter less than said first diameter and said second diameter, said flow restrictor further comprising a deflection surface disposed in said second end portion of said passage defined through said body, said deflection surface being disposed proximate said intermediate, flow control portion of said passage defined through said body, said deflection surface being oriented to impinge a stream of intravenous fluid passing through said intermediate, flow control portion of said passage defined through said body.

2. An intravenous fluid administration system in accordance with claim 1, wherein said deflection surface is generally planar.

3. An intravenous fluid administration system in accordance with claim 1, wherein said intermediate flow control portion of said passage defined through said body is substantially cylindrical and defines a longitudinal axis and wherein at least a portion of said deflection surface is substantially perpendicular to said longitudinal axis.

4. An intravenous fluid administration system in accordance with claim 1, wherein said second end portion of said passage defined through said body of said flow restrictor has a changing diameter along a length thereof.

5. An intravenous fluid administration system in accordance with claim 4, wherein a diameter of said second end portion of said passage defined through said body of said flow restrictor increases distal said intermediate, flow control portion of said passage defined through said body of said flow restrictor.

6. An intravenous fluid administration system in accordance with claim 1, wherein said system further comprises an insert member disposed in said second end portion of said passage defined through said body of said flow restrictor, said insert member having a first end surface wherein said deflection surface comprises said first end surface of said insert member.

7. An intravenous fluid administration system in accordance with claim 6, wherein said insert member further comprises a plurality of radially-extending ribs, said radially extending ribs configured to engage an interior surface of said second end portion of said passage defined through said body of said flow restrictor.

8. An intravenous fluid administration system in accordance with claim 1, wherein said system flow restrictor further comprises a housing disposed about said body of said flow restrictor, said housing being configured for connection with a catheter.

9. An intravenous fluid administration system in accordance with claim 8, wherein said housing defines threads thereon, whereby said housing can be threadably connected to a catheter.

10. An intravenous fluid administration device comprising:
    a flow restrictor defining an intravenous fluid passage therethrough, said flow restrictor having a first end portion configured to be connected to an intravenous fluid reservoir to provide fluid communication between said reservoir and said intravenous fluid passage defined through said flow restrictor, said intravenous fluid passage defined through said flow restrictor comprising a first passage portion, a second passage portion, and an intermediate, flow control passage portion, said second passage portion being disposed distal said first passage portion, and said intermediate, flow control passage portion being disposed between said first passage portion and said second passage portion, said first passage portion of said passage defined through said body having a first diameter at a position proximate said intermediate, fluid control passage portion, said second passage portion of said passage defined through said body having a second diameter at a position proximate said intermediate, fluid control passage portion, and said intermediate, flow control passage portion of said passage defined through said body having a third diameter less than said first diameter and said second diameter, said flow restrictor further comprising a deflection surface disposed in said second passage portion of said passage defined through said body, said deflection surface being disposed proximate said intermediate, flow control passage portion of said passage defined through said body, said deflection surface being oriented to impinge a stream of intravenous fluid passing through said intermediate, flow control portion of said passage defined through said body.

11. An intravenous fluid administration device in accordance with claim 10, wherein said deflection surface is generally planar.

12. An intravenous fluid administration device in accordance with claim 10, wherein said intermediate flow control passage portion of said passage defined through said body is substantially cylindrical and defines a longitudinal axis and wherein at least a portion of said deflection surface is substantially perpendicular to said longitudinal axis.

13. An intravenous fluid administration device in accordance with claim 10, wherein said second passage portion of said passage defined through said body of said flow restrictor has a changing diameter along a length of said second passage portion.

14. An intravenous fluid administration device in accordance with claim 13, wherein a diameter of said second passage portion of said passage defined through said body of said flow restrictor increases distal said intermediate, flow control passage portion of said passage defined through said body of said flow restrictor.

15. An intravenous fluid administration device in accordance with claim 10, wherein said flow restrictor further comprises an insert member disposed in said second passage portion of said passage defined through said body of said flow restrictor, said insert member having a first end surface wherein said deflection surface comprises said first end surface of said insert member.

16. An intravenous fluid administration device in accordance with claim 15, wherein said insert member further comprises a plurality of radially-extending ribs, said radially extending ribs configured to engage an interior surface of said second end portion of said passage defined through said body of said flow restrictor.

17. An intravenous fluid administration device in accordance with claim 10, wherein said flow restrictor further comprises a housing disposed about said body of said flow restrictor, said housing being configured for connection with a catheter.

18. An intravenous fluid administration device in accordance with claim 17, wherein said housing defines threads thereon, whereby said housing can be threadably connected to a catheter.

* * * * *